United States Patent [19]

Broecker et al.

[11] Patent Number: 5,063,194

[45] Date of Patent: Nov. 5, 1991

[54] PALLADIUM CATALYST

[75] Inventors: Franz J. Broecker, Ludwigshafen; Lothar Arnold, Heidelberg; Paul Grafen, Weisenheim, all of Fed. Rep. of Germany

[73] Assignee: BASF Aktiengesellschaft, Ludwigshafen, Fed. Rep. of Germany

[21] Appl. No.: 561,565

[22] Filed: Aug. 2, 1990

[30] Foreign Application Priority Data

Aug. 11, 1989 [DE] Fed. Rep. of Germany ....... 3926561

[51] Int. Cl.$^5$ ...................... B01J 23/60; B01J 23/62; B01J 23/64

[52] U.S. Cl. .................................. 502/314; 502/328; 502/329; 502/339

[58] Field of Search ............... 502/314, 325, 339, 328, 502/329

[56] References Cited

U.S. PATENT DOCUMENTS

| | | | |
|---|---|---|---|
| 3,192,168 | 6/1965 | Grenet et al. | 252/473 |
| 3,715,404 | 2/1973 | Lindlar et al. | 260/642 |
| 3,867,313 | 2/1975 | Brewer | 502/314 |
| 4,001,344 | 1/1977 | Hoffmann et al. | 260/635 M |
| 4,096,095 | 6/1978 | Cairns | 502/314 |
| 4,608,362 | 8/1986 | Drake | 502/243 |
| 4,686,202 | 8/1987 | Broecker et al. | 502/300 |

FOREIGN PATENT DOCUMENTS

| | | |
|---|---|---|
| 0198435 | 10/1986 | European Pat. Off. . |
| 2431929 | 1/1976 | Fed. Rep. of Germany . |
| 2351703 | 12/1977 | France . |
| 871804 | 6/1961 | United Kingdom . |
| 960658 | 6/1964 | United Kingdom ............... 502/339 |
| 1103442 | 2/1968 | United Kingdom . |
| 1578123 | 11/1980 | United Kingdom . |

OTHER PUBLICATIONS

Practical Catalytic Hydrogenation, Freifelder, Wiley-Interscience, 85–126.

Helvetica Chimica Acta, vol. XXXV-446-450 (1952).

*Primary Examiner*—W. J. Shine
*Attorney, Agent, or Firm*—Keil & Weinkauf

[57] ABSTRACT

Palladium catalysts can be obtained by vapor depositing metallic palladium on a carrier, treating the palladium coating with a metallic inhibitor by vapor deposition, and heating the product at from 300° to 800° C., and can be used for the partial hydrogenation of triple bonds to olefinic double bonds.

8 Claims, No Drawings

PALLADIUM CATALYST

Palladium catalysts

The present invention relates to palladium catalysts which can be prepared by vapor-depositing metallic palladium on a carrier, treating the palladium coating with a metallic inhibitor by vapor deposition, and heating the product at from 300 to 800° C.

GB-A-871,804 discloses palladium catalysts which have been treated with solutions of the salts of the metals Zn, Cd, Hg, Ga, In or Tl. These catalysts are suitable for improved selective hydrogenation of acetylene compounds. In addition to this treatment with metal salt solutions, the hydrogenation is carried out in the presence of an amine.

U.S. Pat. No. A3,192,168 discloses a palladium catalyst which contains, as carrier, calcium carbonate and has been partially deactivated using a tin salt. The partial poisoning of the palladium catalyst is effected by impregnation at elevated temperature with tin acetate or tin chloride.

DE-A-2,431,929 discloses palladium-containing catalysts which additionally contain one of the elements zinc or cadmium and at least one of the elements bismuth or tellurium or both zinc and cadmium. The catalyst used is aluminum oxide or pumice. These catalysts are suitable for the preparation of but-2-ene-1, 4-diol by hydrogenating butynediol.

The partial hydrogenation of triple bonds to olefinic double bonds is described in a review of catalyst systems used in industry by M. Freifelder, Practical Catalytic Hydrogenation, Wiley-Interscience, New York, 1971, pp. 84 to 126.

The selective hydrogenation of the triple bond in vitamin and fragrance precursors is usually carried out using Lindlar catalysts, i.e. lead-modified palladium catalysts (Helv. Chim. Acta, 35 (1952), 446–450). In certain cases, these catalysts are deactivated using sulfur compounds (thiodiethylene glycol) (Dutch Application 6,506,928).

In industry, the above-described hydrogenation processes are primarily carried out using the suspension procedure. Thus, the supply of hydrogen is frequently terminated after a certain taken-up of hydrogen has been achieved, thus preventing further hydrogenation.

The inadequate selectivities were disadvantageous in the processes known hitherto.

It was therefore an object of the present invention to develop novel palladium catalysts which overcome the abovementioned disadvantages, and to provide a improved process for selectively hydrogenating compounds containing a triple bond.

We have found that this is achieved by novel palladium catalysts which can be obtained by vapor depositing metallic palladium on a carrier, treating the palladium coating with a metallic inhibitor by vapor deposition, and heating the product at from 300 to 800° C., and by using these catalysts for the selective hydrogenation of triple bonds to olefinic double bonds.

Inhibitors which can be used are tin, lead, zinc, cadmium, antimony and/or bismuth; the latter is preferred. Palladium and the inhibitor are simultaneously or successively deposited on the carrier, and the catalyst precursor obtained in this way is heated, thus forming the actual catalyst.

Suitable vapor deposition techniques are all known coating processes, in particular thermal evaporation. However, flash evaporation, cathode atomization and sputtering can also be used. Thermal evaporation can involve direct or indirect electrical heating Electron-beam evaporation is preferred. In this method, the metal to be evaporated is heated on the surface in a crucible by means of an electron beam so strongly that it evaporates.

The resultant catalyst system comprising carrier, active component and inhibitor is subsequently heated at from 300 to 800° C., preferably from 500 to 700° C., for conditioning. The catalyst foil, mesh or fabric is then expediently shaped to form a monolith or moldings, for example Sulzer ® packing, for installation in the hydrogenation reactor. The desired flow conditions in the reactor can thus be established.

Metallic meshes, foils or fabrics are preferred as the carrier. However, it is also possible to use fabrics of inorganic materials, for example $Al_2O_3$ or $SiO_2$, or combinations of the two. In addition, carbon fiber or plastic fabrics can be employed.

For our objective, the use of a heat resistant stainless steel fabric having the alloy constituents Fe, Cr and Al (description in DIN 17 470) is particularly advantageous. This fabric is first converted into the actual carrier material by conditioning in air at from 800 to 1000° C., preferably 900° C., for from 2 to 20 hours, preferably from 4 to 10 hours.

Vapor deposition on the carrier obtained in this way is carried out continuously in a vacuum vapor deposition apparatus, for example by heating the active component, palladium, at from $10^{-2}$ to $10^{-10}$ mmHg, preferably $10^{-4}$ to $10^{-8}$ mmHg, using an electron beam so strongly that the metal evaporates out of the crucible and condenses on the carrier. The fabric is moved evenly over the evaporation source during the deposition process using a winder. The design of the apparatus ensures that the majority of the vapor stream condenses on the carrier. The inhibitor metal is then applied in a second deposition step, expediently using a second evaporation source.

The monolith catalyst prepared in this way is installed in the hydrogenation reactor, which comprises, for example, a twin-jacket tube. For the catalyst test, a certain amount of hydrodehydrolinalool is initially introduced and passed into the reactor from above via a preheater using a circulating pump. Hydrogen at a certain partial pressure is metered in upstream of the reactor. The product to be hydrogenated then trickles through the catalyst under the $H_2$ partial pressure which has been established. The amount of liquid is chosen to be such that a cross-sectional load of 20 to 80, preferably from 40 to 70 $[m^3/m^2 \times h]$ is achieved. In order to achieve optimum hydrodynamics at the catalyst interface, hydrogen is preferably circulated. The preparation of the catalyst and the selective hydrogenation of the triple bond are described in greater detail in the examples below. The selective hydrogenation of the triple bond is demonstrated using hydrodehyirolinalool (HDHL), which is converted into hydrolinalool (HLIN) in accordance with the reaction equation below.

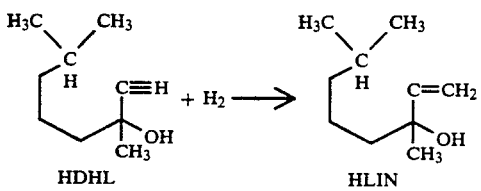

HDHL    HLIN

In this hydrogenation, it is important that the conversion of the HDHL is complete.

EXAMPLES

EXAMPLE 1

Preparation of the catalyst

A smooth stainless steel fabric (material number 1.4767) having a mesh size of 180 μ and a wire diameter of 110 μ is first cleaned in an ultrasound bath and subsequently conditioned in air at 900° C. for 7 hours. A strip of fabric 15 cm wide is clamped on to the winder installed in a UHV vapor-deposition apparatus, and 2 nm of Pd are subsequently deposited continuously under a vacuum of $10^{-6}$ mmHg. By re-winding the fabric, a 0.7 nm Bi coating is deposited in a second step. The catalyst precursor is then conditioned at 600° C. for 30 minutes in an electric furnace, with a heating programme comprising heating to 600° C. over the course of 40 minutes, maintaining this temperature for 40 minutes and then switching the furnace off. After cooling, the catalyst is removed from the furnace and converted into a monolith by waving 41.5 cm of smooth fabric using a ridged roller, placing it together with 38 cm of smooth fabric and rolling up the combination. A monolith catalyst having a volume of 57 cm$^3$ is thus obtained.

EXAMPLE 2

Hydrogenation in a differential reactor

For selective hydrogenation of HDHL to HLIN, the catalyst is installed in a twin-jacket tube with the outer jacket connected to a thermostat. A separator having a gas outlet for the circulation gas and an outlet to the liquid circulation pump is located beneath the reactor. It is also possible to withdraw product samples for analysis. The liquid to be hydrogenated is pumped out of the separator by means of the circulation pump via a preheater to the reactor head. The heater is regulated so that a temperature of 80° C. prevails at the reactor inlet. The hydrogen, which is circulated by pumping in an amount of 67 l(stp)/h and at a partial pressure of 895 mmHg is metered in downstream of the preheater. The circulation pump for the HDHL is adjusted so that a cross-sectional load of 60 [m$^3$/m$^2$×h] is maintained. All but 7.34% of the HDHL is converted into HLIN in 7 hours. The H$_2$ partial pressure is then reduced to 80 mmHg by replacing the pure hydrogen with a gas mixture comprising nitrogen and hydrogen. 100% of the HDHL are converted in 3 hours 20 minutes under this reduced H$_2$ partial pressure of 80 mmHg. At this 100% conversion, a selectivity of 99.3%, based HLIN, is obtained.

EXAMPLE 3

Continuous hydrogenation

The continuous hydrogenation of HDHL to HLIN is carried out in 2 steps using 2 reactors of which the first is operated with product recycling and second without. The hydrogen required is circulated as in Example 2. The hydrogenation reactors comprise twinjacket tubes in which the catalyst is installed in the form of a monolith. A separator equipped with a constant level device and outlets for the circulation gas, the product recycling and product discharge, which is passed directly to the 2nd reactor is located beneath the first reactor. As in Example 2, the recycled product is pumped in the first reactor to the reactor head via the preheater using the circulation pump. HDHL is added continuously upstream of the preheater, and hydrogen is added to the HDHL/recycled product hydrogenation mixture upstream of the preheater by means of the circulation gas pump. The hydrogenation product from the first hydrogenation step is passed to the head of the second reactor via a preheater. As in the first reactor, the circulation gas is again metered in after the preheating. The circulation gas here comprises an H$_2$/N$_2$ mixture having a certain H$_2$ partial pressure. 100% of the HDHL is hydrogenated in the 2nd reactor.

The following reaction conditions apply to the first hydrogenation step:

1st step:
Reaction temperature: 80° C.
H$_2$ partial pressure: 900 mmHg
Space velocity: 1.1 [kg of HDHL/1 of catalyst×h]
Cross-sectional load: 60 [m$^3$/m$^2$×h]
Amount of circulation gas: 1.2 [Nm$^3$/1 of catalyst×h]

Downstream of the first reactor, the hydrogenation product still contains 14.8% of HDHL, which are hydrogenated to completion in the second reactor, with the following reaction conditions being necessary:

2nd step:
Reaction temperature 80° C.
H$_2$ partial pressure 80 mmHg
Space velocity 0.7 [kg of HDHL/1 of catalyst×h]
Cross-sectional load: 60 [m$^3$/m$^2$×h]
Circulation gas composition: 10% of H$_2$, 90% of N$_2$
Amount of circulation gas: 1.2 [Nm$^3$/1 of catalyst×h]

Downstream of the 2nd hydrogenation step, 100% of the HDHL has been converted. The selectivity based on HLIN is 99.5%.

We claim:

1. A palladium catalyst obtained by vapor-depositing metallic palladium on a carrier, treating the palladium coating with a metallic inhibitor by vapor deposition, and heating the product at from 300 to 800° C.

2. A palladium catalyst as defined in claim 1, wherein the carrier is iron-, chromium- and aluminum-containing stainless steel.

3. A palladium catalyst as defined in claim 1, wherein the carrier is in the form of a mesh, fabric or foil.

4. A palladium catalyst as defined in claim 1, wherein the carrier is heated in air at from 800 to 1000° C. before the vapor deposition.

5. A palladium catalyst as defined in claim 1, wherein the catalyst fabric or foil is waved, and a monolith is produced therefrom.

6. A process for the preparation of a palladium catalyst, which comprises vapor depositing metallic palladium on a carrier, treating the palladium coating with a metallic inhibitor by vapor deposition, and thermally treating the product at from 300 to 800° C.

7. A process as defined in claim 6, wherein the metals palladium and bismuth are consecutively evaporated at a reduced pressure of from $10^{-3}$ to $10^{-10}$ bar, and precipitated onto the carrier.

8. A palladium catalyst as defined in claim 1, wherein the metallic inhibitor is tin, led, zinc, cadmium, antimony, bismuth or a mixture of two or more of these metals.

* * * * *